United States Patent
Manne

(10) Patent No.: US 8,052,934 B2
(45) Date of Patent: *Nov. 8, 2011

(54) SCENT DELIVERY DEVICE

(75) Inventor: Joseph Manne, New York, NY (US)

(73) Assignee: J.B. Scientific, New York, NY (US)

( * ) Notice: Subject to any disclaimer, the term of this patent is extended or adjusted under 35 U.S.C. 154(b) by 525 days.

This patent is subject to a terminal disclaimer.

(21) Appl. No.: 12/108,017

(22) Filed: Apr. 23, 2008

(65) Prior Publication Data

US 2008/0267833 A1    Oct. 30, 2008

Related U.S. Application Data

(60) Division of application No. 10/875,098, filed on Jun. 23, 2004, now Pat. No. 7,376,344, and a continuation-in-part of application No. 10/408,142, filed on Apr. 7, 2003, now Pat. No. 7,203,417.

(60) Provisional application No. 60/458,185, filed on Mar. 27, 2003, provisional application No. 60/439,588, filed on Jan. 13, 2003, provisional application No. 60/370,881, filed on Apr. 8, 2002.

(51) Int. Cl.
*A62B 7/08*    (2006.01)
*F24F 6/00*    (2006.01)

(52) U.S. Cl. .......... 422/123; 422/125; 392/390
(58) Field of Classification Search ........... 422/123, 422/125; 390/392; 392/390
See application file for complete search history.

(56) References Cited

U.S. PATENT DOCUMENTS

| | | |
|---|---|---|
| 2,999,428 A | 9/1961 | Mariani |
| 5,565,148 A | 10/1996 | Pendergrass, Jr. |
| 5,805,768 A | 9/1998 | Schwartz et al. |
| 5,972,290 A | 10/1999 | De Sousa |
| 6,476,984 B1 | 11/2002 | Ringdahl |
| 6,713,024 B1 | 3/2004 | Arnell et al. |
| 6,808,289 B2 * | 10/2004 | Reed .................. 362/198 |
| 7,203,417 B2 | 4/2007 | Manne |

FOREIGN PATENT DOCUMENTS

WO    WO 0012143 A1 *    3/2000

* cited by examiner

*Primary Examiner* — Kevin Joyner
(74) *Attorney, Agent, or Firm* — Lucas & Mercanti, LLP

(57) ABSTRACT

The scent delivery device employs a housing and scent generator which selectively releases scent. The housing is mounted on a counter and allows a user to selectively sample a variety of scent. The scent travels to the user's nose by diffusion.

4 Claims, 16 Drawing Sheets

SCENT DELIVERY DEVICE

CROSS-REFERENCE TO RELATED APPLICATIONS

This application is a divisional application of U.S. patent application Ser. No. 10/875,098, which is a continuation-in-part of U.S. patent application Ser. No. 10/408,142 filed Apr. 7, 2003, which in turn claimed the priority of U.S. Provisional Patent Application Nos. 60/370,881 filed Apr. 8, 2002; 60/439,588 filed Jan. 13, 2003; and 60/458,185 filed Mar. 27, 2003.

BACKGROUND OF THE INVENTION

1. Field of the Invention

The present invention relates to scent and, more particularly, to a scent delivery device which allows for sampling of scent. The device allows a user to breathe a variety of scents by means of diffusion through the open air.

2. Art Related to the Invention

A scent delivery device is disclosed in International Patent Application Publication No. WO 99/01793 published Jan. 14, 1999. Such a device employs a case which houses scent containers, a conduit which connects the case to the nose of the user and a fan which moves scented air from the case through the conduit and to the nose. Such a device constitutes a closed air system.

The device of the '793 Publication relies on convection or flow of scented air through a closed conduit system to move the scented air to the user's nose. Other prior art systems have also relied on fluid flow to move scent to a user's nose. A number of these prior art systems are open air systems which move the scent through the open air by means of a fan or pump. However, such systems tend to be bulky and not adaptable to miniaturization.

There is a need for a miniaturized stationary scent delivery device that can be easily allowing a user to sample a scent by diffusion.

SUMMARY OF THE INVENTION

The present invention is a stationary scent delivery device to provide scent to a user's nose or, more specifically, to the olfactory receptors of the user's nose, by means of diffusion.

Broadly, the scent delivery device of the present invention comprises:

a stationary housing having a delivery area; and a scent generating means for selectively generating scent, said scent generating means housed in said housing, wherein the scent is generated at said delivery area and travels by diffusion to the user's nose, the user's nose being placed in close proximity to the delivery area.

The term scent as used in the specification and claims means the effluent that is perceived by the olfactory organs.

The intended purpose of the present invention is to provide a device that houses a wide variety of scents and allows a user to sample each of the scents without having the user move. Such a device is intended to be placed on a store countertop and allows the user to select a plurality of scents, one at a time for sampling. However, the device of the present invention can be adapted to be mounted or placed onto any stationary object such that it places the device into close proximity of a user's nose.

The phrase stationary housing, as used in the specification and claims, means a stand or other device which is adapted to be placed on, or mounted to, a stationary object and house the scent generating means thereby allowing the scent generating means to be placed in close proximity to the user's nose.

Examples of stationary objects include, desk top computers, lap top computers, televisions, interior of an automobile, a desk, workstation, a seat, such as one used in an airplane, theatre, train or automobile. The specific location of the device is mounted on the stationary object such that, when the person is stationary at or near the object, the device is located in close proximity to the user's nose. It will be understood that stationary object means an object that is stationary with respect to a user, e.g. an automobile is stationary with respect to its passenger.

Adapted to be mounted means that the device can be fixed onto the object in either a permanent manner by, for example, bolting the device to the object; or in a semi-permanent manner, by using a clamp, such as a spring clamp, so as to allow the user to readily move the device from one stationary object to another.

The phrase close proximity means about 30 inches or less (75 cm or less). This has been found to be an acceptable distance to allow the scent to reach the nose of the user by diffusion.

Diffusion is a recognized natural phenomenon of the spreading or scattering of material. In the present invention, diffusion moves the scent from the scent generating means to the nose by the ambient air, or the natural flow of air that surrounds the user and the scent delivery device. Generally, the nose of the user will be placed above the scent delivery device and thus the scent will flow upward to the nose. Optionally, the flow of scent by diffusion can be assisted by means of a heater or a fan. As is recognized, hot air generally travels upward. The fan employed in the present invention is small and is not intended to cool the user but to provide a gentle current or direction to the air so as to aid in the diffusion of scent to the nose.

The scent generating means is small and can take on a number of embodiments.

In a first embodiment, the scent generating means of the present invention comprises a support affixed to the housing; one or more scent sources mounted on the support to selectively provide scent to the delivery area; and a release means for selectively releasing scent from the scent sources directly to the delivery area.

In this first embodiment of the scent generating means, the support is a silicon chip, disk, or thin plastic film, one side of which is affixed to the housing, the other side of which allows for scent to be released.

In this first embodiment of the scent generating means, the release means for selectively releasing scent to the user's nose acts on the scent source to release the scent. The means includes a micro-mechanical system (MEMS), tape or other means, to release the desired scent to or in the delivery area. The release means can be activated manually or electronically.

The scent source can be of many types for this first embodiment. The scent source can be a micro-container which contains scent molecules in a liquid or gel form. In this embodiment, the container holding the scent molecules is normally, closed, however, when the release means is activated, the container is selectively opened to allow the scent molecules to diffuse into the delivery area towards the olfactory nerve receptors of the nose.

The scent source can also be scent molecules which are microencapsulated in heat sensitive capsules. Under conditions of normal environmental temperatures, the microcapsules remain intact and the scent molecules are contained within. They cannot be sensed by the olfactory receptors.

However, the means for releasing the scent selectively heats the microcapsules so that the desired scent source is heated and a certain portion of the scent molecules are liberated and allowed to diffuse to the olfactory receptors. As soon as the microcapsules cool, no more scent molecules are liberated from the microcapsules.

In a second embodiment of the scent generating means, one or more scent containers are mounted on a delivery means housed in said housing and the delivery means selectively delivers scent from the scent containers directly to the delivery area.

The scent containers are placed near or adjacent to the delivery area one at a time, or more than one at a time. The delivery means moves the scent containers to the delivery area. The scent containers in this second embodiment can be the same as those for the first embodiment.

In this second embodiment, the container holding the scent molecules is normally closed, however, when it is moved into position in the delivery area, it is selectively opened to allow the scent molecules to diffuse into the delivery area towards the olfactory nerve receptors of the nose. Where microencapsulated scent molecules are used, these molecules are moved to the delivery area and then heated or activated to release the scent.

A first embodiment of the delivery means comprises:
(1) an endless belt rotatably mounted in said housing;
(2) each of said scent containers are mounted on said endless belt, a port in each of said scent containers through which scent travels when said port is open, and an elastic flap closing said port to prevent scent from leaving said scent container when said flap is down and allowing scent to travel through said port when said flap is up;
(3) an arm mounted in said housing which rides over said flap pushing said flap down when said containers rotate in one direction and when said containers rotate in the other direction said arm pushes said flap up; and
(4) a reversible motor mounted in said housing and rotating said endless belt in both said one and said other direction, thereby selectively releasing scent from said scent container.

The endless belt can be replaced with a disc that rotates, thus, instead of a linear movement, the scent container has a circular movement. The belt can be a chain.

A second embodiment of the delivery means comprises:
(1) a can mounted in the housing, said can having an open end which faces said user and a closed end;
(2) each of said scent containers housed in said can, a port in each of said containers through which scent travels when said port is open, said port facing said open end of said can;
(3) a rotatable disk mounted against said open end of said can and closing said open end of said can, said disk having one opening which corresponds in size to said port of said scent container; and
(4) a reversible motor mounted in said housing and connected to said disk and rotates said disk to align said opening in said disk with said port in said scent container to release scent from one of said containers and to close the other scent containers, thereby selectively releasing scent from said scent container.

A third embodiment of the delivery means comprises:
(1) a tube mounted in the housing, said tube having an open end which faces said delivery area and a closed end;
(2) each of said scent containers movably mounted in said tube, a port in each of said scent containers through which said scent travels when said port is open, said port facing said open end of said tube; and
(3) a reversible motor mounted in the housing and moving said scent containers individually into and out of said tube through the open end of said tube to place said port of a moved scent container in the delivery area, thereby selectively releasing scent from said tubes.

A fourth embodiment of said delivery means comprises:
(1) capillary tubes which are bundled together and attached to said housing in such a way that the other end of each of said capillary tubes is open and in the delivery area and the one end of each of said tubes is sealed, the scent containers are formed by said capillary tubes;
(2) removable caps are mounted on the other end of the tubes; and
(3) a reversible motor attached to said removable caps to selectively open and close said caps to selectively release scent from said tubes.

A fifth embodiment of the delivery means comprises:
(1) an endless belt rotatably mounted in said housing;
(2) each of said scent containers mounted on said endless belt, a port in each of said scent containers through which scent travels when said port is open, and a hinged cap closing said port to prevent scent from leaving said scent container when said cap is down and allowing scent to travel through said port when said cap is up;
(3) a motorized arm mounted on said housing at said delivery area for opening and closing said cap; and
(4) a reversible motor mounted on said housing and rotating said endless belt in both said one and said other direction.

A sixth embodiment of the delivery means comprises:
(1) an endless belt rotatably mounted in said housing;
(2) a scent housing mounted in said housing for placing scent on said endless belt;
(3) a cleaner housing mounted in said housing for removing scent from said belt; and
(4) a reversible motor for moving said belt so as to move scent on said belt from said scent housing to the delivery area and then to a cleaner housing.

A seventh embodiment of the delivery means comprises:
(1) a matrix in said housing in which each of said scent containers are held;
(2) a dynamic alloy wire which is affixed to a cap of said scent containers; and
(3) means to activate said dynamic alloy wire to open said cap and allow scent to escape from said container and deactivate said dynamic alloy wire to close said container, said means being controllable, to allow for selection of which cap to open.

An eighth embodiment of the delivery means comprises:
(1) a circular endless tube rotatably mounted in the housing in which said scent is housed in compartments, a port in each of said compartments through the wall of the tube through which scent travels when said port is open, and an elastic flap closing said port to prevent scent from leaving said compartments when said flap is down and allowing scent to travel through said port when said flap is up;
(2) an arm mounted in said housing which rides over said flap pushing said flap down when said tube rotates in one direction and when said tube rotates in the other direction said arm pushes said flap up; and
(4) a reversible motor mounted in said housing and rotating said tube in both said one and said other direction, thereby selectively releasing scent from said compartments.

A ninth embodiment of the delivery means comprises:
(1) an endless belt rotatably mounted in said housing, microencapsulated scent mounted on said endless belt;
(2) a heater mounted near said belt for heating the scent to be released from said belt; and
(3) a reversible motor for moving said belt so as to move scent on said belt from said heater to release scent.

A tenth embodiment of the delivery means comprises:

(1) an endless belt rotatably mounted in said housing, each of said scent containers mounted on said endless belt;

(2) a push button extending through said housing that is capable of lifting said flap up when said push button is depressed and is capable of pushing said flap down when said push button is released; and (3) a rotatable dial extending through said housing and connected to said endless belt for rotating said endless belt.

In any embodiment, a fan or heater can be employed to assist diffusion and provide a current of air on which the scent molecules travel to the nose.

The housing can further include affixing means for affixing the housing to a stationary object, the means to affix can include bolts, screws or a clamp which allows for the housing to be releasably affixed to the stationary housing. The affixing means can be attached directly to the housing or can include an arm or flexible gooseneck which allows for movement and positioning of the housing while affixing the housing to the stationary object.

BRIEF DESCRIPTION OF THE DRAWINGS

These and other aspects of the present invention may be more fully understood by reference to one or more of the following drawings.

DETAILED DESCRIPTION OF THE INVENTION

Figure 1:
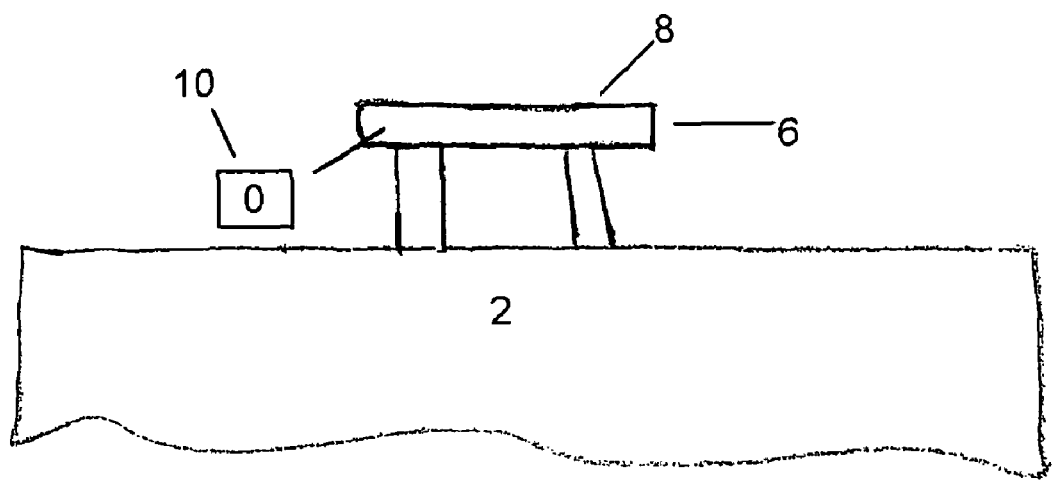
FIG. 1 illustrates a housing of the invention positioned on a countertop.

FIG. 1 illustrates counter 2 having a housing 6 mounted thereon. Housing 6 has a delivery area 8, shown in more detail in FIG. 2.

Control unit 10 allows the user to select which scent to sample. The user places their nose over delivery area 8 and breathes the scent which is generated in delivery area 8 by diffusion.

Figure 2:
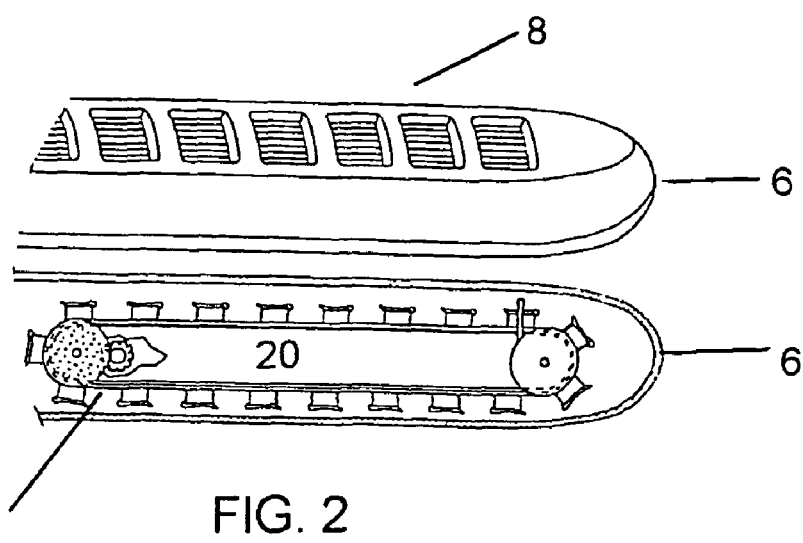
FIGS. 2, 2A and 3A-3F illustrate the first embodiment of the delivery means and its operation.
Figure 2A:
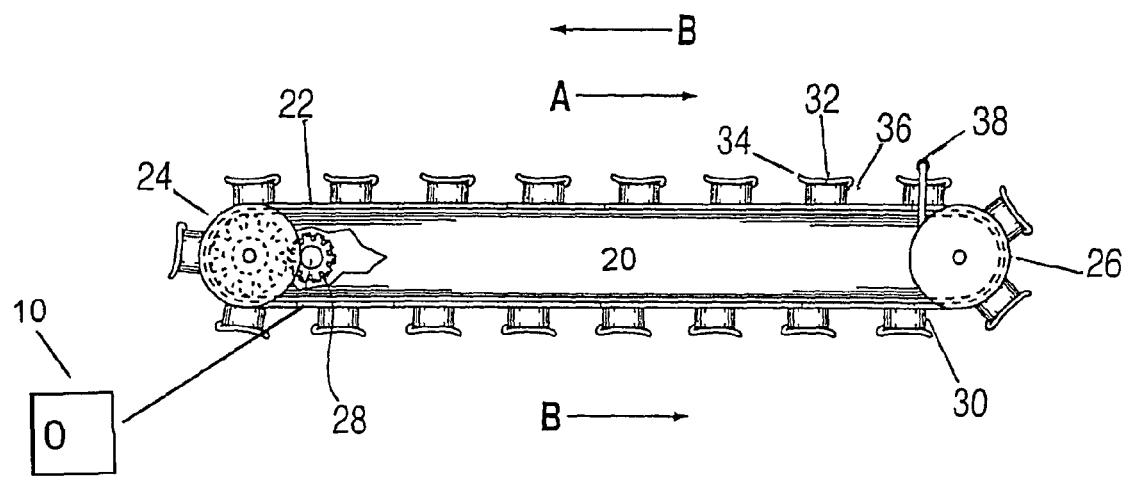

FIGS. 2 and 2A illustrate housing 6 having frame 20 with endless belt 22 mounted thereon. Belt 22 rotates on wheels 24 and 26 while motor 28 provides the power to cause wheel 24 to rotate, thereby moving belt 22. Scent container 30 is mounted on belt 22. Each container 30 has a hole in top surface 32 and flap 34 which is affixed to the front of container 30 at point 36. Arm 38 is affixed to frame 20 at the end of frame 20 that resides near or under the nose of user 8. Arm 38 is spring biased to allow it to move upward and away from frame 20 in a direction perpendicular to the long axis of frame 20.

Motor 28 is reversible such that it can cause belt 22 to move in forward direction A or reverse direction B, and is controlled by control unit 10.

The term motor as used herein refers to a motor that is driven by any conventional means, e.g., electrically driven, gas driven or mechanically driven. The mechanically driven motor can include a rotating arm or dial that extends outside housing 6 so as to allow a user to manually rotate rotating arm to drive belt 22.

Figure 3A:
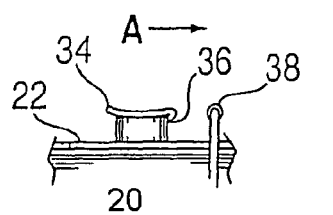
Figure 3B:
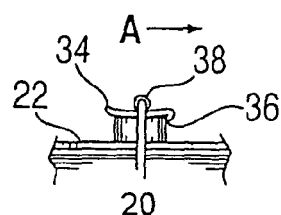

Arm 38 rides over flap 34 when belt 22 moves in forward direction A as shown in FIGS. 3A and 3B. Since flap 34 is affixed to scent container 30 at point 36 and arm 38 is spring biased, when the front of scent container 30 makes initial contact with arm 38, it pushes arm 38 up and over flap 34, thereby pushing flap 34 downward against scent container 30 and maintaining hole in top surface 32 closed.

Figure 3C:
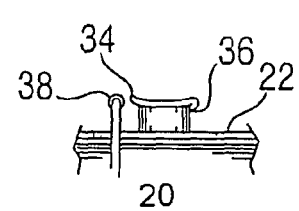
Figure 3D:
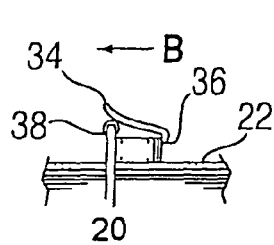
Figure 3E:
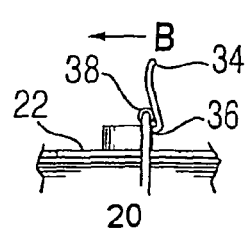
Figure 3F:
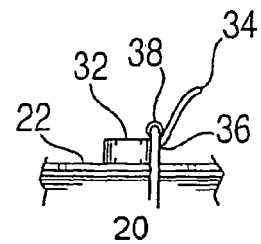

In FIG. 3C, belt 22 is stopped. In FIGS. 3D and 3E, belt 22 travels in reverse direction B. Because flap 34 is not affixed at the back of container 30 and because arm 38 is spring biased, arm 38 gets under flap 34 when belt 22 operates in reverse direction B. In FIG. 3F, belt 22 stops and scent escapes from container 30 through the hole in top surface 32. Since arm 38 is mounted at the end of frame 20 which is at delivery area 8, the user will smell the scent.

Because flap 34 is biased to a closed position as shown in FIG. 3A, flap 34 will close the hole in top surface 32 when belt 22 moves in forward direction A after being opened as shown in FIG. 3F. Thus, after the position in FIG. 3F, when belt 22 moves forward, container 30 and flap 34 will assume the position shown in FIG. 3C when arm 38 is moved to behind container 30 as shown in FIG. 3C.

As an alternative to the embodiment in FIGS. 2, 2A and 3A-3F, arm 38 can be spring loaded to ride off of top 34 and connected to a dynamic alloy wire to bring arm 38 down into a position as shown in FIG. 3C. Then, movements of FIG. 3D-3F are employed to open container 30. After scent has been delivered, belt 22 is moved in direction of arrow B to close container 30. The dynamic alloy wire is deactivated and a spring then pulls arm 38 out of the path of container 30. In this embodiment belt 22 can move in either direction to position container 30 in position to be opened by arm 38. Other conventional means can be employed to move arm 38 into and out of engagement with container 30.

Figure 4:
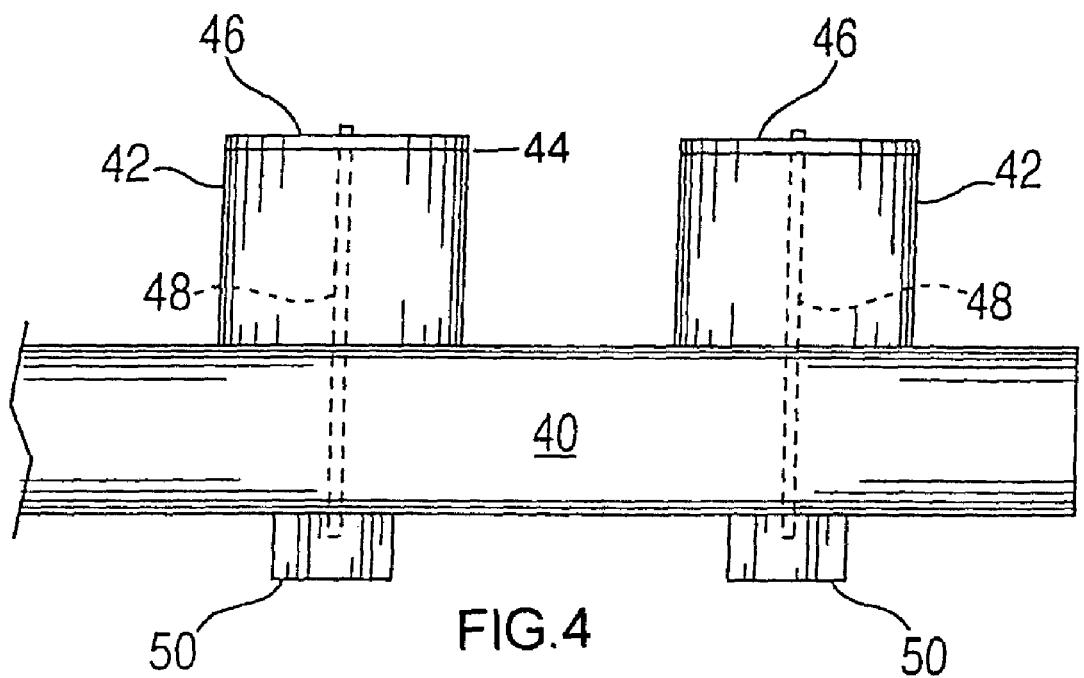
FIGS. 4 and 5 illustrate a side and top view of the second embodiment of the delivery means.
Figure 5:
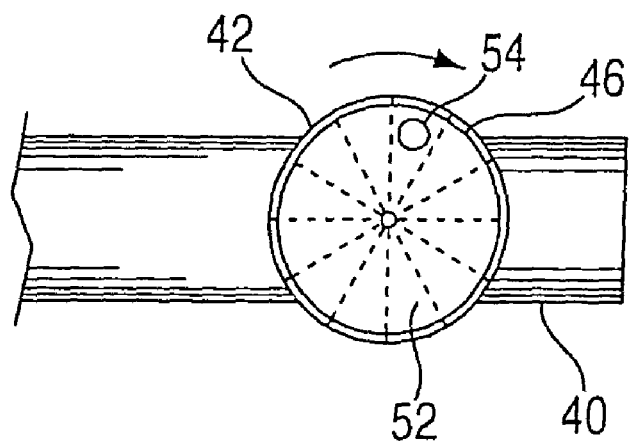
Figure 6A:
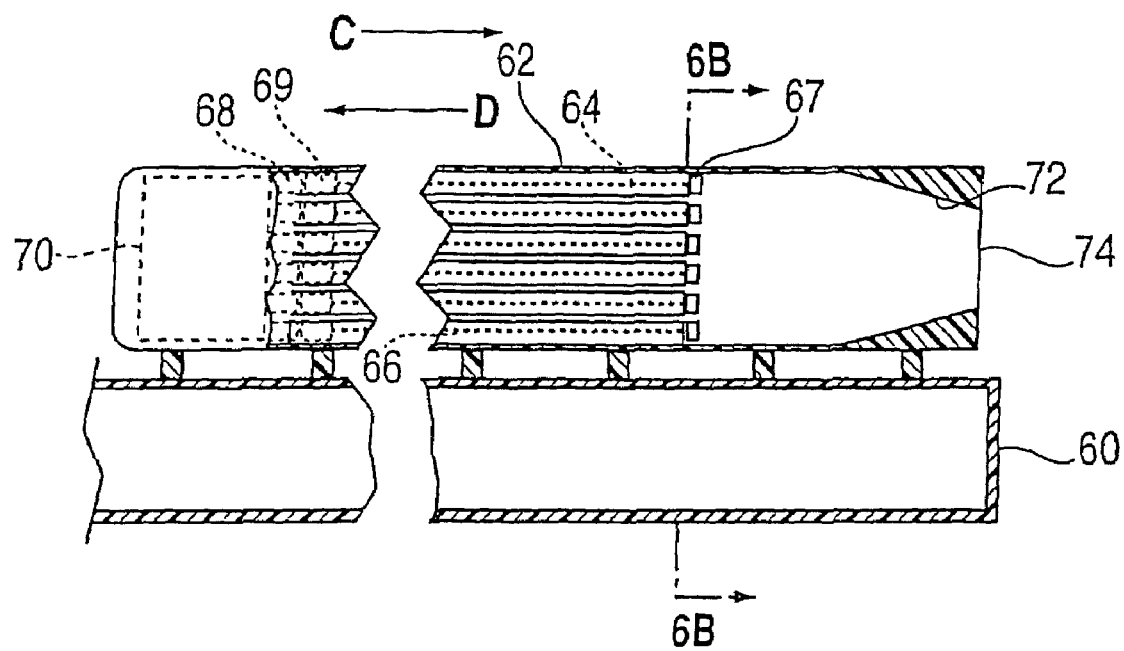
FIGS. 6A, 6B, 7A and 7B illustrate the third embodiment of the delivery means.
Figure 6B:
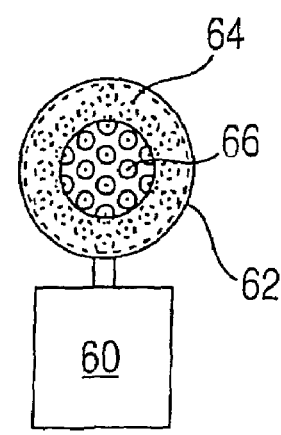

FIGS. 4 and 5 illustrate a second preferred embodiment of the delivery means of the present invention. In FIG. 4, frame 40 has one or more cans 42 mounted thereon. Frame 40 is mounted on or part of the housing. Top 44 of cans 42 is open but sealed by disk 46. Disk 46 is connected by shaft 48 to motor 50. Motor 50 is affixed to the bottom of boom 40. Motor 50 rotates disk 46 by means of shaft 48. Motor 50 can be an electrical, motor or a hand operated motor or dial which rotates disk 46.

As shown in FIG. 5, cans 42 contain a plurality of scent containers 52. Disk 46 has hole 54. Each scent container 52 is open at top 44 such that when hole 54 resides over one of scent containers 52, the scent will travel upward through hole 54.

Suitably, one of the wedges in which said container 52 resides can be empty or closed such that there is a point where hole 54 can be positioned and no scent will escape cans 42.

Figure 7A:
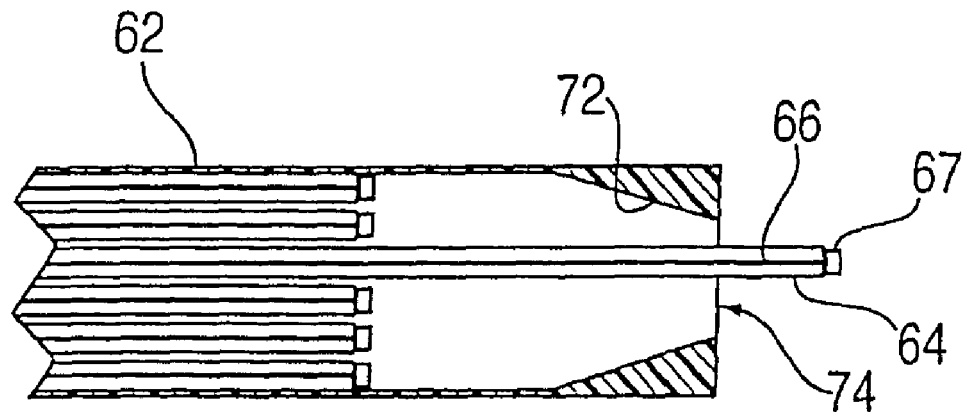
Figure 7B:
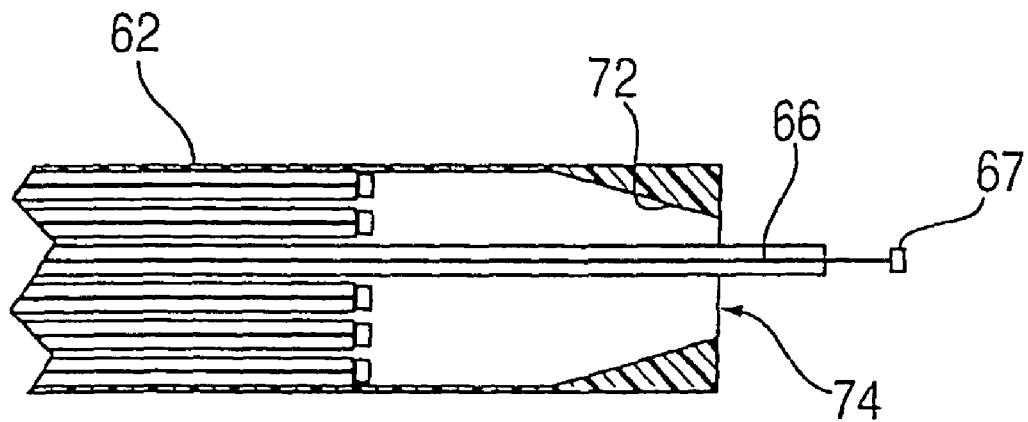

FIGS. 6A, 6B, 7A and 7B illustrate a third embodiment of the delivery means of the present invention. In FIG. 6, frame 60 has tube 62 mounted thereon. Frame 60 is attached to or part of the housing. Scent containers 64 are mounted in tube 62 and each contain solid wick 66. Cap 67 is mounted on end of wick 66 and closes container 64 when wick 66 is retracted inside container 64. Pistons 68 are mounted at the rear of each scent container 64 while pistons 69 are mounted at the rear of wicks 66. Motor 70 controls the forward and rearward movements of pistons 68 and 69. The front of tube 62 has a conical shaped section 72 such that when one of pistons 68 pushes one of containers 64 forward in direction C, the forward moving container 64 is guided out through hole 74, delivery area at the end of tube 62. The length of travel of piston 68 is such to move the end of container 64 with cap 67 outside of tube 62. Once cap 67 of container 64 has exited through hole 74 as shown in FIG. 7A, piston 68 stops as does the forward movement or container 64. Next, piston 69 is activated by motor 70 to cause wick 66 with cap 67 thereon to extend wick 66 outside of tube 62 as shown in FIG. 7B, and thereby release scent.

Motor 70 can move pistons 68 and 69 in rearward direction D thereby moving wick 66 back into container 64 and container 64 back into tube 62. Motor 70 can be electrical or hand operated in a conventional manner.

Each scent container has a wick positioned therein on which a scent has been absorbed or an equivalent arrangement. Wick 66 is stiff to allow it to move itself and cap 67 forward and backward.

Figure 8:
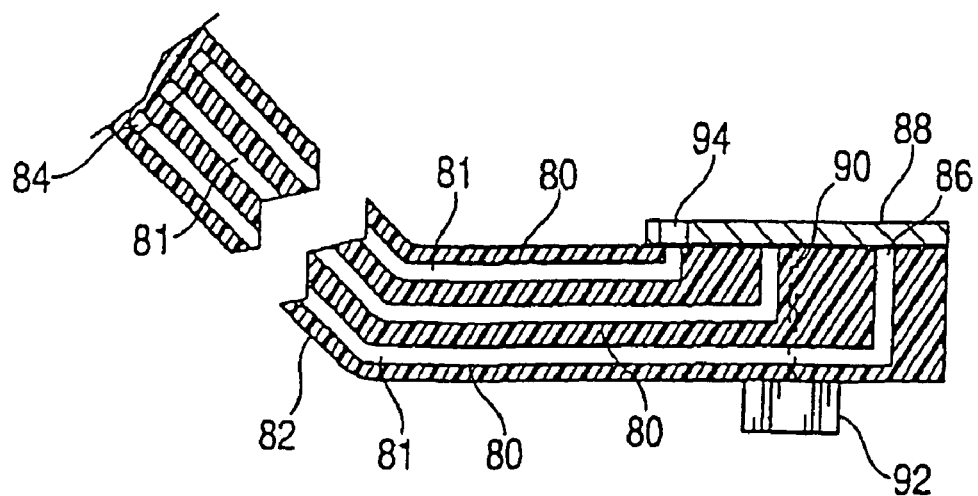
FIG. 8 illustrates the fourth embodiment of the delivery means.

FIG. 8 illustrates a fourth embodiment of the delivery means of the present invention. In FIG. 8 capillary tubes 80 contain scent 81 and are housed in frame 82. Frame 82 is housed in or part of the housing. Each tube 80 has a capped end 84 and an open end 86. Disk 88 is mounted on and rotatable about shaft 90. Motor 92 rotates shaft 90 thereby causing disk 88 to rotate. Disk 88 is designed and operated similar to disk 46 of FIG. 4 such that disk 88 has hole 94 which rotates so as to open and close end 86 of tube 80. Motor 92 can be electrical or hand operated such as a hand dial that rotates disk 88.

Figure 9A:
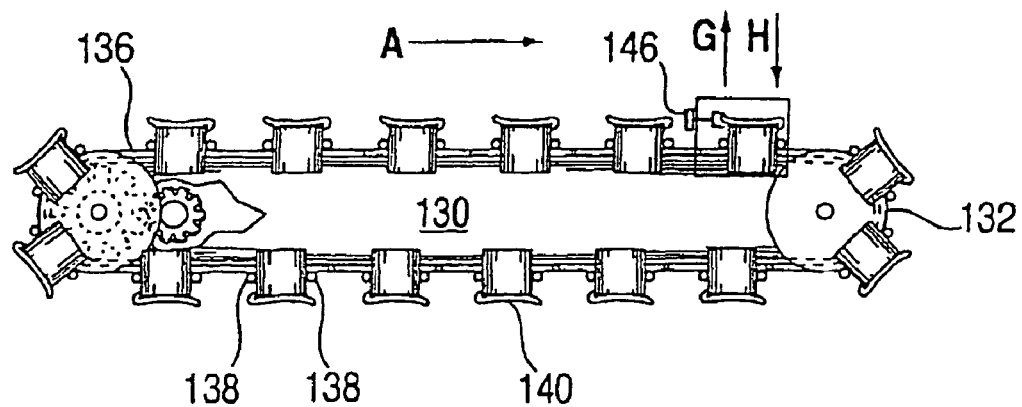
FIGS. 9A and 9B illustrate the fifth embodiment of the delivery means.
Figure 9B:
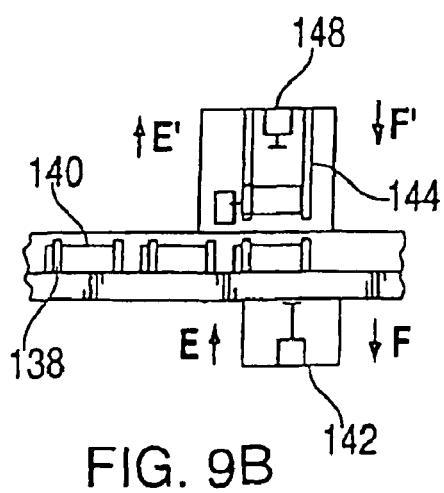

FIGS. 9A and 9B illustrate the fifth embodiment of the delivery means of the present invention. FIG. 9A is a side view while FIG. 9B is a top view. Frame 130 has end 132 where scent is released. Frame 130 is part of or affixed to the housing. Endless belt 136 is driven in a forward direction A by wheels and motor arrangement as shown in FIG. 2. Mounted on the side of belt 136 are clips 138 which hold container 140 by pressure against belt 136.

Piston 142 moves both forward E to push containers 140 out of clip 138 and into corral or delivery area 144. Piston 142 then retracts. Activator 146 moves upward G to open the cap of container 140 and downward H to close container 140. Piston 148 moves forward $F^1$ to push container 140 back into clip 138 and then retracts in direction $E^1$ to allow for unobstructed movement of belt 136.

By opening and closing container 140 in this way, scent is released. The cap of container 140 is hinged. The concentration of the scent is controlled by the degree of opening of the cap. Activator 146 varies in its position of opening and closing.

Frame 130 can include a temperature sensor to determine how far open the container should be. This is based on vapor pressure for the scent employed in the device.

Figure 10:
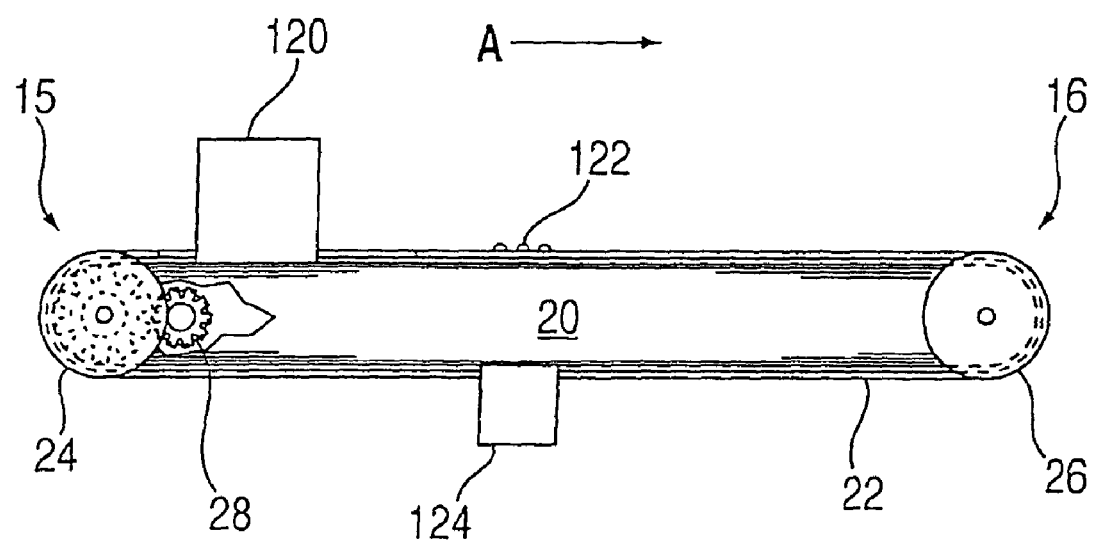
FIG. 10 illustrates the sixth embodiment of the delivery means.

FIG. 10 illustrates the sixth embodiment of the delivery means wherein a frame similar to the one depicted in FIG. 2 is illustrated with two ends 15 and 16. Specifically, frame 20 has endless belt 22 mounted on wheels 24 and 26 with motor 28 providing power to rotate belt 22 in direction A. In this embodiment, housing 120 releases scent molecules 122 onto belt 22 and belt 22 carries scent molecules 122 to under the nose of user 8. End 16 of frame 20 is positioned in the delivery area such that when scent molecules 122 are in the delivery area, scent will travel to the user's nose by diffusion. When bell 22 is continued to be rotated scent molecules 122 will pass through housing 124 and housing 124 cleans belt 22 to remove scent molecules 122 from belt 22. Housing 120 can release a plurality of scents into one location of the belt thereby synthesizing scent on the spot. Housing 120 can employ any conventional means to deposit the scent onto the belt, for example with a jet type process.

Figure 11:
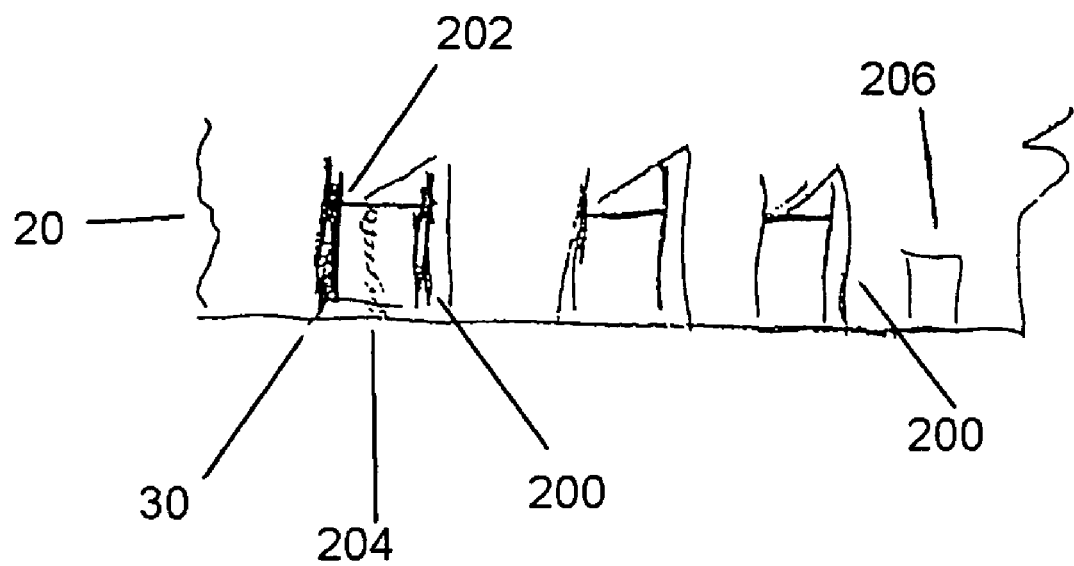
FIG. 11 illustrates the seventh embodiment of the delivery means.

FIG. 11 illustrates the seventh embodiment of the delivery means wherein containers 30 are housed in a body portion of frame 20 with dynamic alloy wire 200 connected to cap 202. Each cap 202 has spring 204 which biases cap 202 in a closed position. Microprocessor 206 is connected to each wire 200 and controls the activation and deactivation of wire 200, thereby controlling the opening and closing of cap 202.

Figure 12:
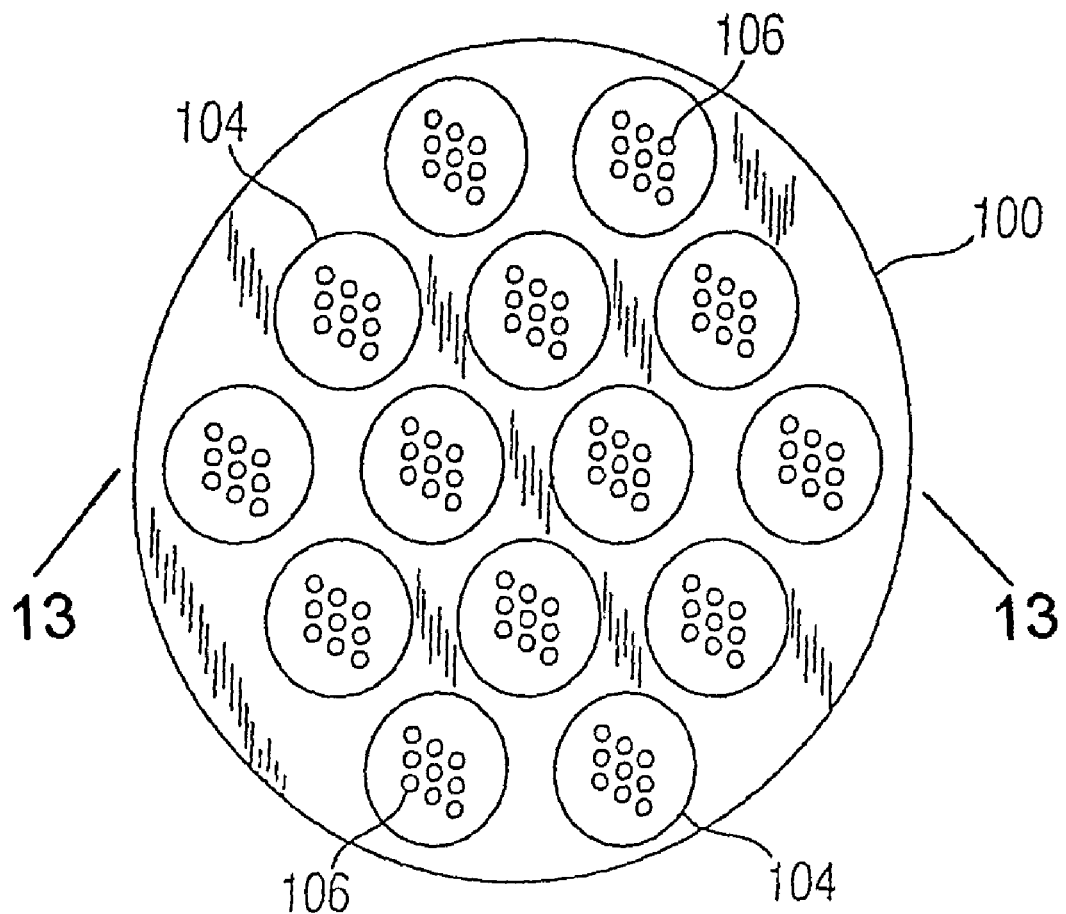
FIGS. 12 and 13 illustrate a top view and cross-section of a disc of the invention.
Figure 13:
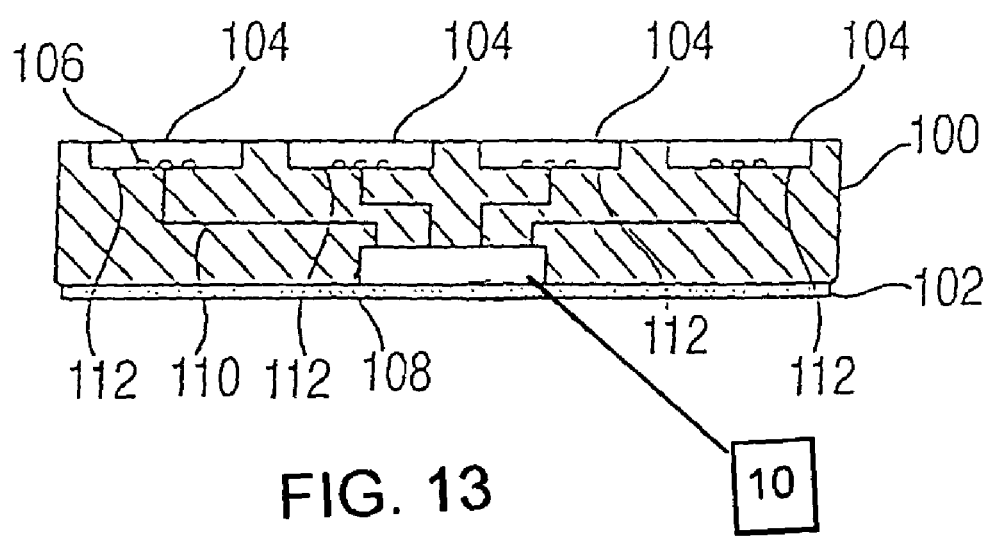

FIGS. 12 and 13 illustrate a disk 100 having adhesive 102 on one side of disk 100 and cavities 104 with microcapsules 106 housed therein on the other side of disk 100. Microprocessor 108 is attached by wires 110 to heater 112. Microprocessor 108 is controlled by control unit 10 which communicates in a conventional way to microprocessor 108 to control the scent that is released. Heater 112 not only causes the release of scent from microcapsule 106, but can also cause an air current by the fact that the air is heated to above ambient temperatures, thereby causing an upward flow of air.

Instead of heater 112 to activate release of scent, a means can be employed to open and close cavities 104. Specifically, each open end of cavity 104 can be capped with a micromechanical cap, a microelectrical cap, or a molecular cap. These different types of caps are made in a conventional manner and operate in a conventional way to open and close cavity 104, thereby controlling release of scent. Heater 112 can still be employed to promote movement of the scent molecules and provide a current of air to carry the scent to the user's nose. Microprocessor 108 is used to control the opening and closing of cavity 104.

It will be understood by those of skill in the art that disc 100 can be a silicon chip into which capillary tubes or wells have been etched into the chip. These wells and tubes, often referred to as nanochannels, are often on the order of a few microns (micrometers) in diameter. They are able to house scent molecules because the scent molecules are smaller than the diameter of the nanochannels.

Figure 14:
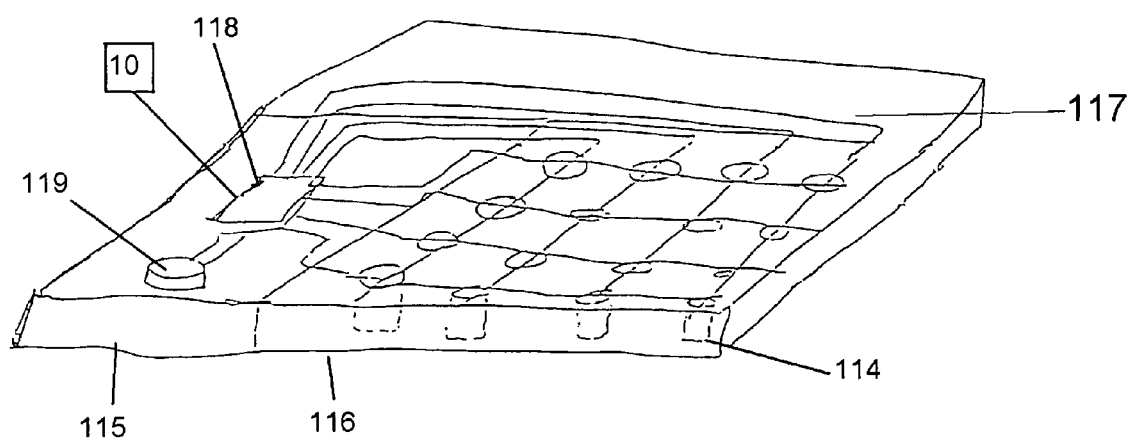
FIG. 14 illustrates a silicon chip of the invention.

In FIG. 14 such a silicon chip is illustrated. In this embodiment, a plurality of microcapsules or cavities 114 are embedded within microchip 115. Each microcapsule 114 contains a small quantity of a concentrated scent-producing substance. Each capsule 114 may have a cap to prevent unintended release of the scent. Alternatively, the scent-producing substance may be a solid. Bottom side 116 has adhesive for affixing to the portable housing.

Microcapsules 114 are preferably arranged in a matrix grid on the microchip 115 as shown in FIG. 14. A grid of electrodes 117 are overlaid on or electrically connected to microcapsules 114 and connected by wires or other conductors to microprocessor 118. Microprocessor 118 is housed on microchip 115. Battery 119 supplies power.

The user selects a specific scent by pre-programming microprocessor 118 or by using a control unit 10. Microprocessor 118 energizes the proper horizontal and vertical electrodes 117 for microcapsule 114 containing the selected scent. A heating element at the intersection of electrodes 117 heats up the specific microcapsule to release the scent. Alternatively, a catalyst or other chemical could be released or electrically activated at the intersection point to generate the desired scent. Or a piezoelectric lid may be positioned over each scent cavity, the lid opening when electrically energized to release the scent.

Control unit 10 is a conventional microcontrol that controls the motors and switches that run the scent generator means.

It will be recognized that more than one cavity 114 or 104 can be opened at one time thereby allowing for the synthesis of scent by the device itself.

Figure 15:
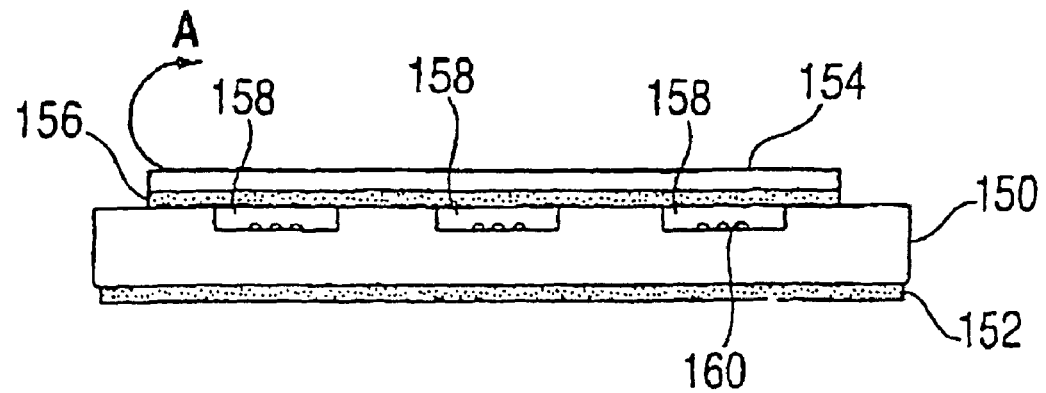
FIGS. 15 and 16 illustrate a cross-section and top view of the tape of the invention.
Figure 16:
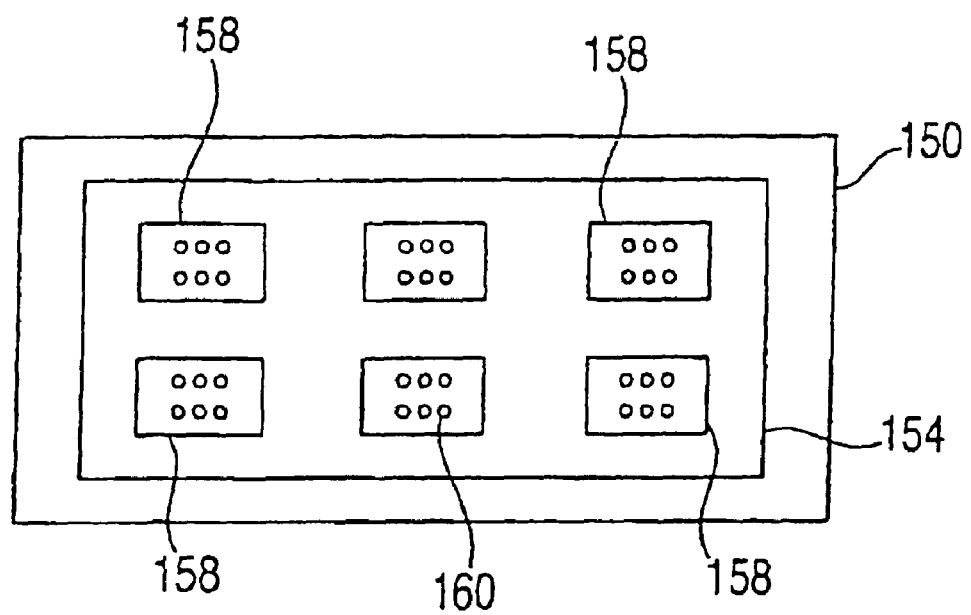

FIGS. 15 and 16 illustrate one embodiment of the present invention wherein a tape is employed to affix the scent generating means to the housing. Tape 150 has adhesives layer 152 on one side and cover tape 154 on the other side. Cover tape 154 adheres to the top of tape 150 because of adhesive layer 156. In or on tape 150 are pockets 158 of scent 160. By peeling back cover tape 154 in the direction of arrow A, pockets are opened and scent 160 can escape. By replacing cover tape 154 over opened pocket 158, scent 160 is no longer released from pocket 158, thus stopping the diffusion of scent to the user.

Using the devices in FIGS. 12-16, the device must be closer to the user's nose than in the other devices disclosed herein because the quantity of scent molecules generated by the device are less.

Figure 17:
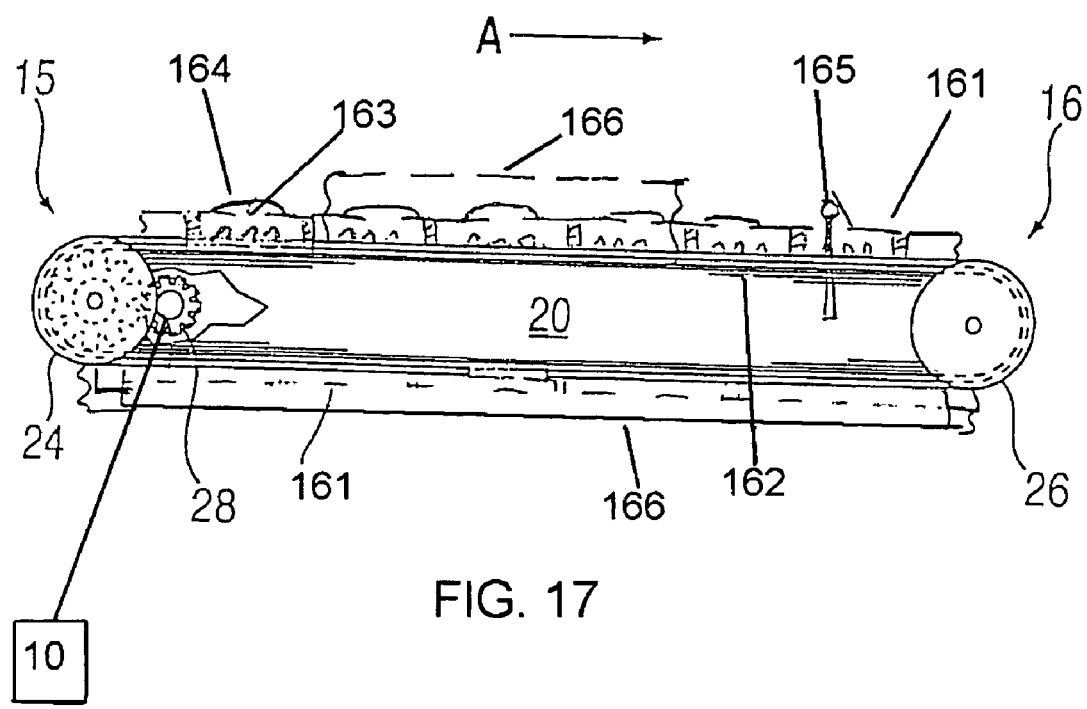
FIG. 17 illustrates the eighth embodiment of the delivery means of the present invention.

FIG. 17 illustrates the eighth embodiment of the present invention where a wheel-motor arrangement 24, 26, 28, as shown in FIG. 2, is employed and tube 161 is compartmentalized into individual compartments that house scent 162. Each compartment has port 163 and flap 164 which is biased in a closed position. Arm 165 rides over flap 164 when tube 161 moves in the direction of arrow A. When tube 161 is moved in a direction opposite arrow A, arm 165 rides under flap 164 and opens flap 164 allowing scent to escape from the compartments. The operation and movement of this embodiment works similar to the first embodiment as shown in FIGS. 3A-3F. Protection tube 166 is stationary and affixed to housing 20. Tube 161 moves about wheels 24, 26 driven by motor 28 both forward and reverse. Control unit 10 controls the movement of motor 28.

Figure 18:
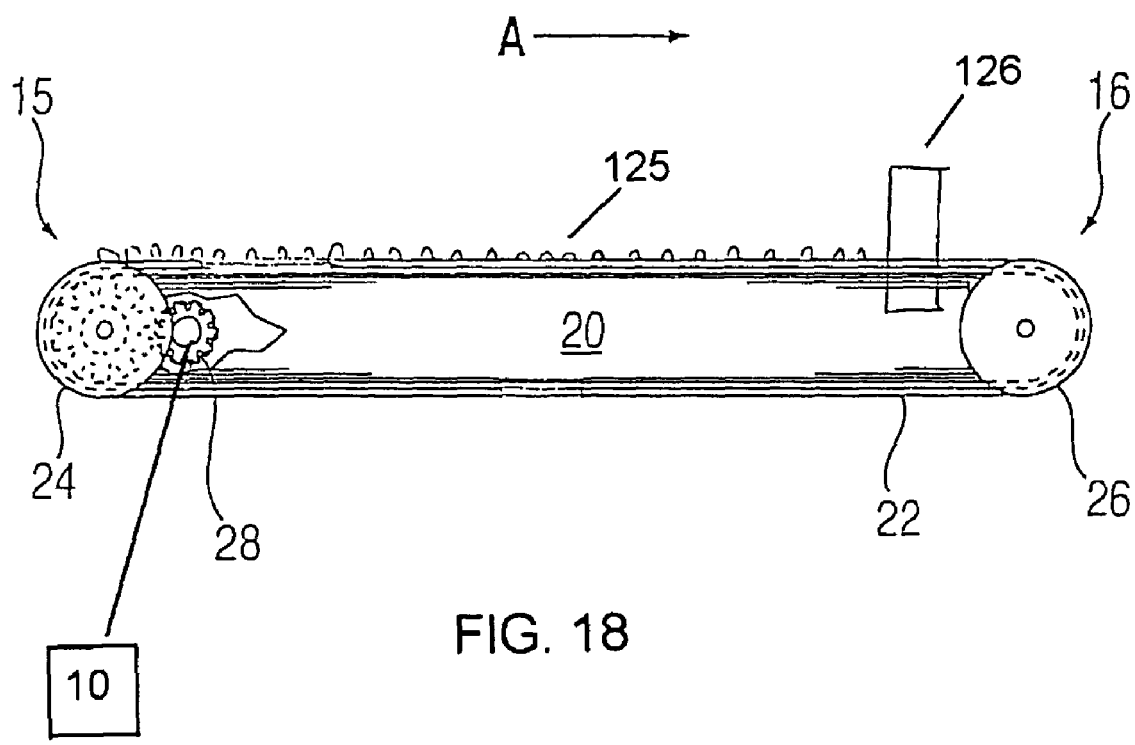
FIG. 18 illustrates the ninth embodiment of the delivery means of the present invention.

FIG. 18 illustrates the ninth embodiment where endless belt 22 is pre-formed with microencapsulated scent 15 adhered to belt 22. Housing 16 has either a heater to open the capsules or a mechanical arm that provides shear to break the microcapsules and release the scent. The control unit 10 of the devices is used to both rotate the belt to position the correct scent in housing 126 and to activate the heater or arm to release the scent. Depending on the type of microcapsule, either a heater or an arm is employed. Belt 22 can have either multiple scents or a single scent.

Figure 19:
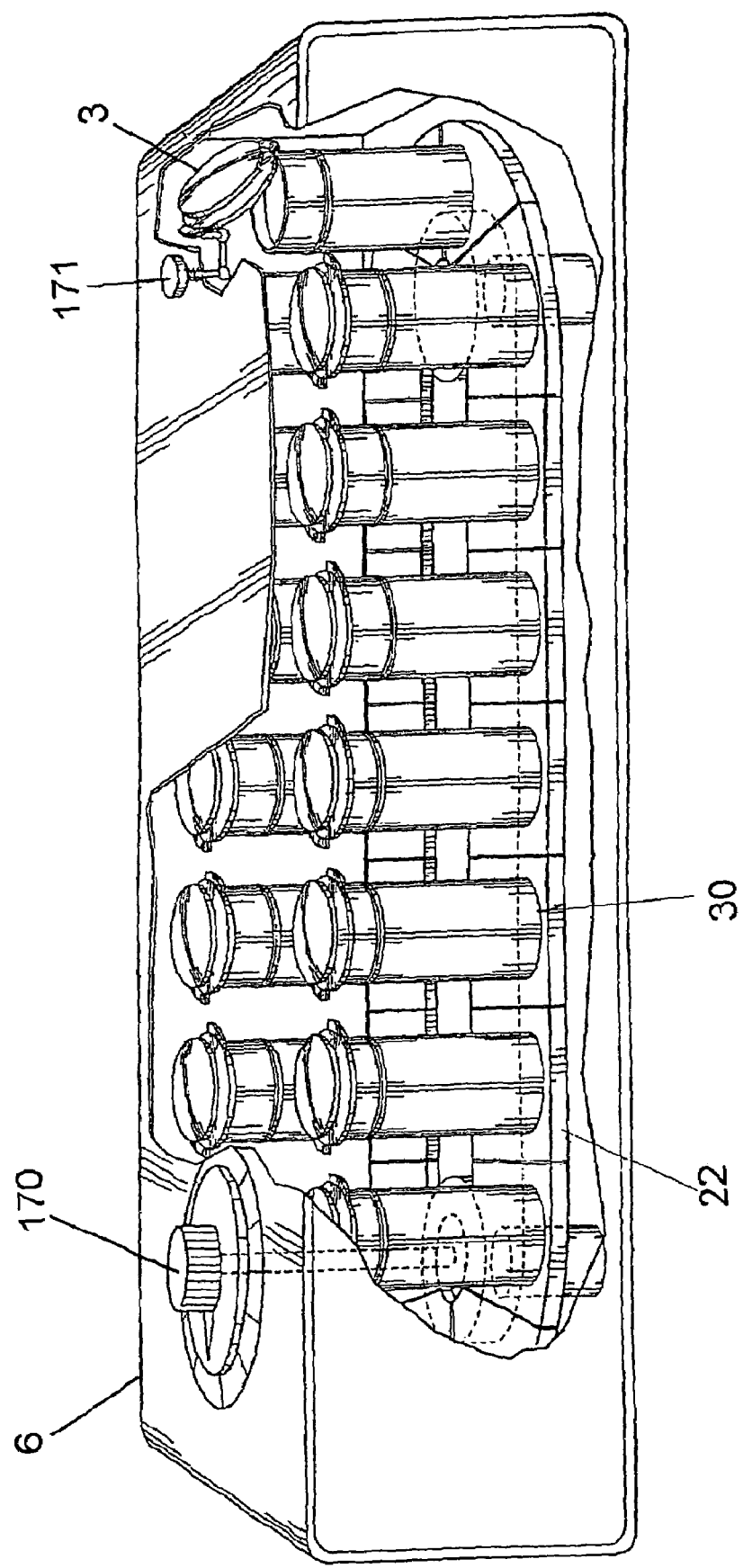
FIG. 19 illustrates the tenth embodiment of the delivery means of the present invention.

FIG. 19 illustrates a tenth embodiment of the delivery means of the present invention. Scent containers 30 are mounted on rotatable endless belt 22 within housing 6. Rotatable dial 170 extends through the surface of housing 6 in order to provide a mechanism to manually rotate endless belt 22 and scent containers 30. Push button 171 extends through the surface of housing 6 in order to provide a mechanism to manually open flap 34 of a scent containers 30 that is located beneath push button 171. When push button 171 is depressed, flap 34 of the corresponding scent container 30 is lifted to release the scent trapped within scent container 30. When push button 171 is released, flap 34 of scent container 30 is lowered to trap the scent within scent container 30. It will be appreciated that a plurality of push buttons 171 can be positioned throughout housing 6 to allow for flaps 34 of multiple scent containers 30 to be lifted simultaneously.

It is important to tightly close flap 34 in order to facilitate the tight closing, a spring and/or piston can be employed. If flap 34 is not tightly closed, scent can escape.

Figure 20A:
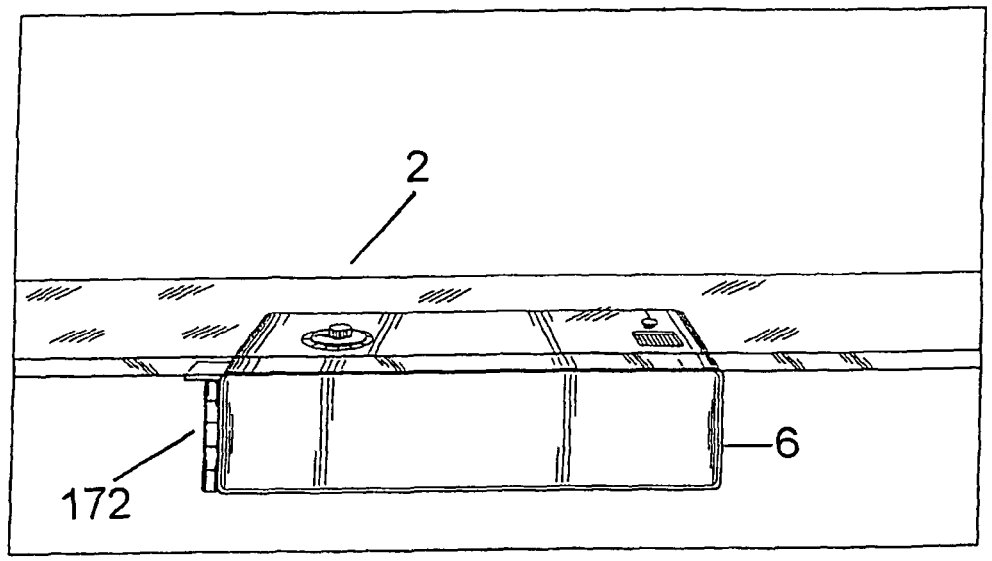
FIGS. 20A and 20B illustrate the tenth embodiment of the present invention rotatable from a counter.
Figure 20B:
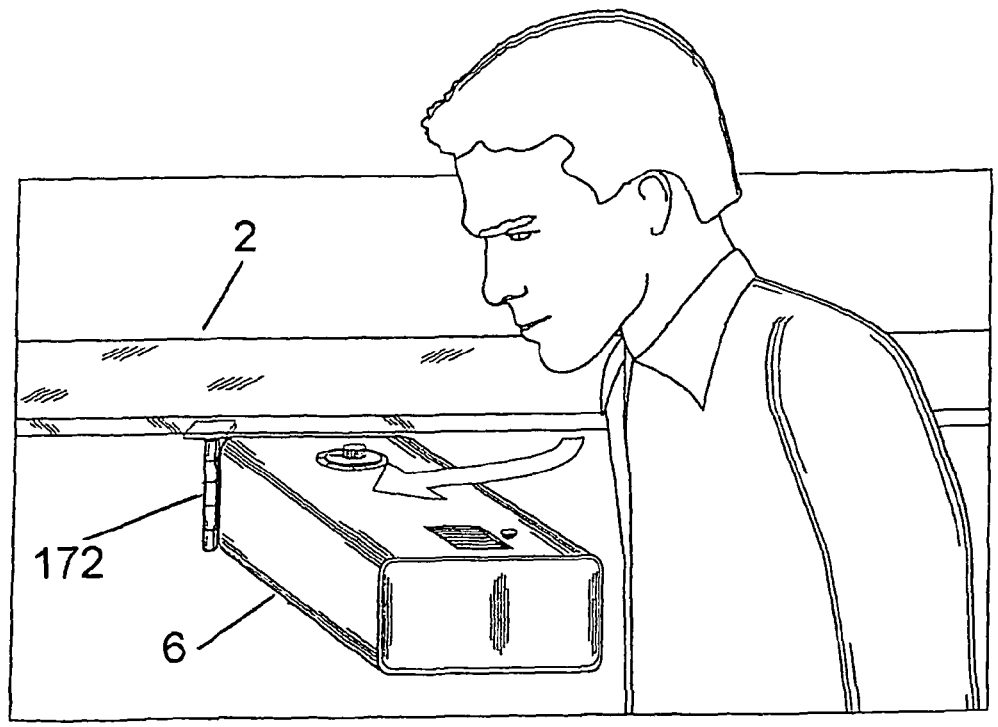

FIGS. 20A and 20B illustrate an attachment of the present invention to a position beneath store counter 2. Rotating mechanism 172 is attached to housing 6 to provide a rotation of the entire device from a hidden position beneath counter 2 to an extended position from counter 2. Rotating mechanism 172 provides for the conservation of space when the device is not in use. Rotating mechanism 172 can also be attached to counter 2 at a position above counter 2 to provide a rotation of the entire device above counter 2.

It will be appreciated that dial 170 can be replaced with an electrical motor, associated sensors and a microcontroller to facilitate movement of the belt. Push button 171 and its associated mechanism can likewise be driven by an electrical motor, microcontroller and sensors.

Figure 21:
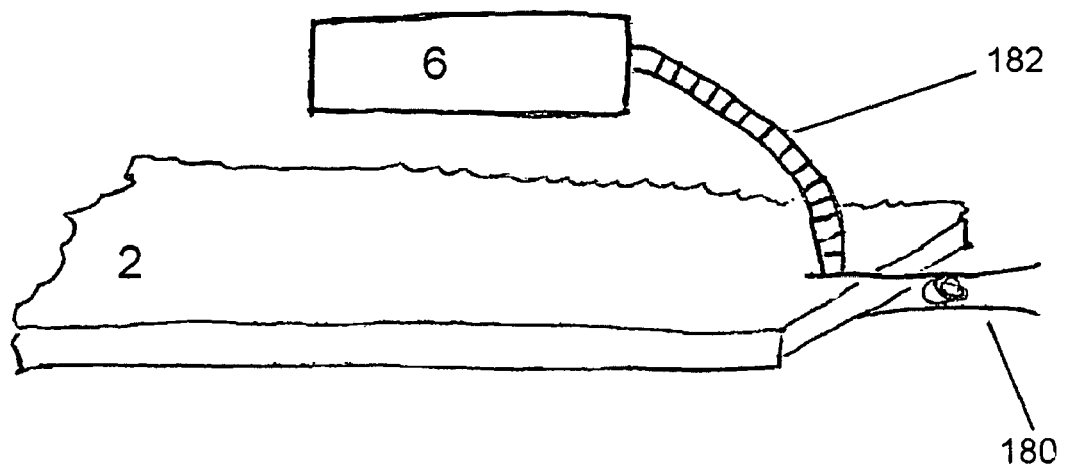
FIG. 21 illustrates a spring clamp and a gooseneck to releasably affix the housing to the stationary object.

As shown in FIG. 21, the scent delivery device comprises housing 6 releasably affixed to counter 2 by means of clamp 180 and flexible gooseneck 182. Flexible gooseneck 182 allows a user to move housing 6 while clamp 180 remains affixed to counter 2. Clamp 180 is a spring clamp which allows a user to remove the device and affix the device to other stationary objects.

A fan or heater can be mounted in association with the present invention to create a current of air directed towards the nose or face of the user and thereby assist in the diffusion of scent molecules to the nose. Suitable fans include axle fans. Such fans are conventional fans which are small in size. One such fan measures 1½ inches×1½ inches by 1 inch (4×4×2.5 cm) and moves 7 cubic feet of air per minute (0.2 cum).

The present invention has been found to work well at a distance of less than or equal to about 30 inches (75 cm) from the user.

In the embodiments that employ a moving belt or moving disc to open and close the scent containers, sensors are employed to provide feedback as to the location of the scent containers to allow the process to control the placement and to know the location of the scent container.

The processor and the battery for the device of the present invention can be made external to the device such that they are housed and connected by conventional wires to the device.

It will be understood that the claims are intended to cover all changes and modifications of the preferred embodiments of the invention herein chosen for the purpose of illustration which do not constitute a departure from the spirit and scope of the invention.

What is claimed is:
1. A scent delivery device comprising:
(a) a housing with a delivery area; and
(b) a means for selectively generating scent housed in said housing at said delivery area, wherein said scent travels by diffusion from said delivery area to the nose of the user when the nose of the user is placed in close proximity to said delivery area, said means for selectively generating scent having:
(b1) one or more scent sources which are mounted in said housing and adapted to release scent, said scent source is one or more scent containers each having:
(b1i) a port in each of said scent containers through which scent travels when said port is open; and

(b1ii) an elastic flap closing said port to prevent scent from leaving said scent container when said flap is down and allowing scent to travel through said port when said flap is up;

(b2) a delivery means for selectively releasing scent from said scent sources and delivering said released scent to said delivery area, said delivery means for selectively releasing said scent comprises:

(b2i) an endless belt rotatably mounted in said housing, each of said scent containers mounted on said endless belt;

(b2ii) a push button extending through said housing that is capable of lifting said flap up when said push button is depressed and is capable of lowering said flap when said push button is released; and (b2iii) a rotatable dial extending through said housing and connected to said endless belt for rotating said endless belt.

2. The device of claim 1 wherein housing adapted to be mounted on a countertop.

3. The device of claim 1, further comprising a clamp for releasably affixing said housing to a stationary object.

4. The device of claim 3 wherein said housing is connected to said clamp by means of a gooseneck.

* * * * *